United States Patent [19]

Blumenfeld et al.

[11] 4,059,618
[45] Nov. 22, 1977

[54] TETRAHALOGEN XYLYLENE DIACRYLATES, TETRAHALOGEN XYLYL ACRYLATES, PENTAHALOGEN BENZYL ACRYLATES, AND SUBSTITUTED ACRYLATES

[75] Inventors: Georg Blumenfeld, St. Augustin; Hermann Richtzenhain, Much, Schwellbach; Wilhelm Vogt, Cologne-Sulz; Norbert Volkommer, Troisdorf, all of Germany

[73] Assignee: Dynamit Nobel Aktiengesellschaft, Troisdorf Bez. Cologne, Germany

[21] Appl. No.: 589,958

[22] Filed: June 24, 1975

[30] Foreign Application Priority Data

June 26, 1974 Germany .............................. 2430629
Feb. 27, 1974 Germany .............................. 2408468

[51] Int. Cl.² ........................................... C07C 69/54
[52] U.S. Cl. .................................. 560/221; 526/292; 526/296; 526/329.3; 526/329.4
[58] Field of Search ..................... 260/486 R

[56] References Cited

U.S. PATENT DOCUMENTS

| 2,375,301 | 5/1945 | Joyce | 260/486 R |
|---|---|---|---|
| 2,861,098 | 11/1958 | Di Sanza | 260/486 R |
| 3,418,360 | 12/1968 | Schulz | 260/486 R |

*Primary Examiner*—Paul J. Killos
*Attorney, Agent, or Firm*—Burgess, Dinklage & Sprung

[57] ABSTRACT

Compounds of the formula:

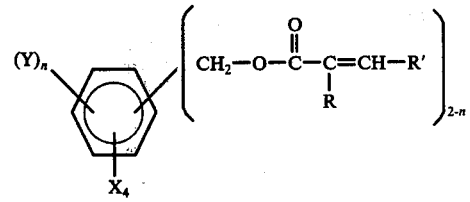

wherein:
each X is chloro or bromo
Y is methyl or bromo
$n$ is 0 or 1
each of R and R' is hydrogen or methyl.

The compounds are produced by contacting an alkali salt of R'—(CH=C(R))—COOH with tetrahalogen xylene chloride or xylylene dichloride or pentabromobenzylchloride in a polar solvent. The compounds are useful as comonomers and as cross linking agents in polymerization of unsaturated compounds.

8 Claims, No Drawings

TETRAHALOGEN XYLYLENE DIACRYLATES, TETRAHALOGEN XYLYL ACRYLATES, PENTAHALOGEN BENZYL ACRYLATES, AND SUBSTITUTED ACRYLATES

The subject matter of the present patent application is tetrahalogen xylylene diesters, tetrahalogen xylyl esters and pentahalogen benzyl esters of the formula, e.g.

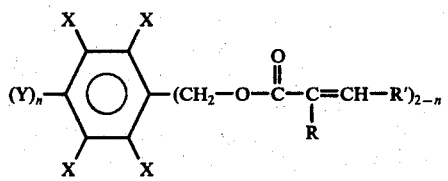

in which X represents bromine or chlorine, Y methyl or bromine, $n = 0$ or 1, and R and R' each represents hydrogen or a methyl group, as well as a method of preparing same.

Of the tetrahalogen xylylene diacrylates and dimethacrylates, the para compounds are preferred on account of the easy availability of brominated or chlorinated p-xylylene dichloride.

Since the unsaturated acyl radical can be derived from acrylic acid, methacrylic acid or crotonic acid, both of the radicals R and R' can be hydrogen, or one can be a methyl group and the other hydrogen.

The preparation of the unsaturated esters can be accomplished by the reaction of halogenated aromatic chloromethyl compounds of the formula $(Y)_nC_6X_4(CH_2Cl)_{2-n}$, in which X and Y and n have the above meaning, representing tetrahalogen xylylene dichlorides, pentahalogen benzyl chlorides or tetrahalogen xylyl monochlorides, as the case may be, with the alkali salts of $\alpha,\beta$-unsaturated acids, acrylic acid, methacrylic acid or crotonic acid in polar solvents which are miscible to at least some degree with water. The preparation of the unsaturated esters of the invention— formulated on the example of pentabromobenzyl acrylate— is accomplished in accordance with the following outline:

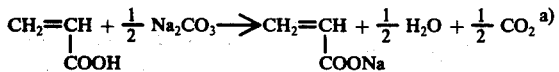

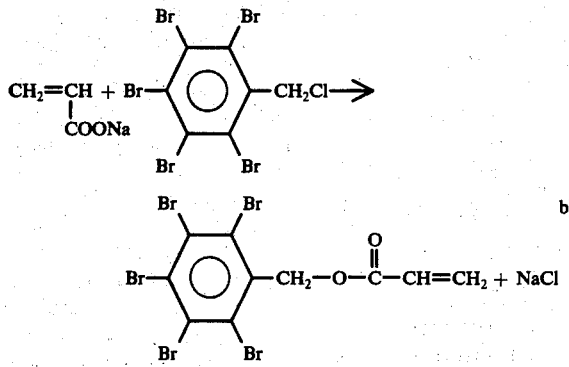

In a polar organic solvent, unsaturated carboxylic acids of the formula R'—CH=C(R)—COOH, wherein R and R' have the same meaning as above, are transformed to the alkali salts by the addition of, for example, alkali carbonates or bicarbonates, or alkali hydroxides or tertiary amines such as triethyl or tributyl amine. Of the alkali compounds the carbonates are greatly preferred, although the hydroxides, bicarbonates or, in some cases, the alkali alcoholates, particularly the methylates, can be used also. Then the particular chloromethyl compound is added to a stoichiometric excess of at least 1 mole %, e.g. 1 to 10 mole-%, of the alkali salt of the unsaturated carboxylic acid and reacted at 50°–150° C to form the ester, in the presence of a polymerization inhibitor.

The formation of a salt between the unsaturated acid and the alkali carbonate takes place generally in the temperature range of 10°–80° C, preferably at room temperature, a polymerization inhibitor being added first, and the alkali carbonate being then added portionwise, with stirring, so as to prevent excessive foaming (evolution of $CO_2$). After the chloromethyl compound has been added, the mixture is heated to the reaction temperature in the range from 50° to 150° C, preferably from 80° to 130° C, and allowed to react until virtually complete transformation has been achieved. The reaction time is between 0.5 and 5 hours. The reaction can be pursued by the quantitative determination of the alkali chloride that is produced, which is accomplished by Mohr's method of chloride determination.

Suitable polar solvents are, for example, alcohols of $C_1$ to $C_4$, glycols of up to 6 carbon atoms, ether alcohols of up to 6 carbon atoms, tetrahydrofuron, dioxane, dimethoxyethane, dimethylformamide, dimethylacetamide, N-methylpyrrolidone and dimethylsulfoxide. Ethyleneglycol monomethyl ether is used preferentially. Methyl glycol is a preferred glycol.

Suitable inhibitors are hydroquinone, p-benzoquinone, pyrocatechol, 4-tert.-butylpyrocatechol, hydroquinone monomethyl ether, and 2,4,6-tri-tert.-butylphenol. Hydroquinone is used preferentially. $Na_2CO_3$ or $K_2CO_3$ are used preferentially as the alkali carbonate. The stoichiometric excess of 1 to 10 mole-% of the alkali salt of the acid over the pentabromobenzyl chloride or tetrabromoxylylene dichloride, as the case may be, is intended to assure a complete transformation of these last-named starting products. The excess amounts of alkali acrylate or methacrylate can easily be separated together with the alkali chloride when the reacted mixture is worked up.

Alkali carbonate and unsaturated acid can be added in equivalent amounts; however, with the aim of avoiding the formation of undesired by-products, such as products of the addition of the ethylene glycol monomethyl ether used as the solvent onto the C=C double bond of the acrylic or methacrylic acid, or polymers formed by vinyl polymerization taking place during the esterification, it has been found advantageous to use the unsaturated acid in a slight stoichiometric excess above the alkali carbonates used for the salt formation, so that the reaction mixture will have an acid reaction during and after the salt formation. In this manner the alkali-catalyzed addition of methyl glycol onto the acid double bond is prevented and the phenolic inhibitor can produce an adequate action.

At the end of the reaction, the reaction products are in solution, with the exception of the alkali chloride and small amounts of already polymerized or cross-linked acrylic or methacrylic esters, as the case may be. The undissolved products can be separated by filtration or centrifugation. Upon the cooling of the filtrate, the esters of Formula 1 crystallize in high yields and adequate purity. They are separated, washed chloride-free with water, and dried preferably at room temperature. For the isolation of the esters, the reaction solution (after separation of substances remaining undissolved at elevated temperature, according to the circumstances) can also be poured into water and the reaction products precipitated in this manner. Such a procedure may be recommendable in the case of tetrabromoxylylenedimethacrylate, which is somewhat slower in crystallizing.

One special embodiment of the reaction of the invention is the use of methyl glycol as the solvent and of sodium hydroxide in an approximately 50% aqueous solution. The latter is added gradually to an up to 10 mole-% excess of $\alpha,\beta$-unsaturated acid in methyl glycol, which gives the mixture an acid reaction during and after the salt formation, and prevents the alkali-catalyzed addition of methyl glycol onto the acid double bond. The reaction of the sodium salts of $\alpha,\beta$-unsaturated acid with, for example, tetrachloroxylyl chlorides and tetrachloroxylylene dichlorides in methyl glycol and water takes place upon refluxing. The starting products and the end products are in solution during the heating, except for the NaCl that forms in the reaction. Upon cooling, the esters of Formula I crystallize predominantly, in high yields and in high purity, and can be refined by recrystallization.

It has been found that the excess of unsaturated acid above the caustic soda solution used for the salt formation not only prevents the alkali-catalyzed addition of methyl glycol, for example, onto the acid double bond, but also permits the full effect of the phenolic polymerization inhibitors to be exercised in the further reaction. For example, in the preparation of tetrachloro-o-xylylenediacrylate in the presence of excess acrylic acid (Example 12), no polymerization of the reaction product was found, whereas in the experiment without an excess of acrylic acid (Example 25) under otherwise identical conditions, 35% of the calculated amount of tetrachloro-p-xylylenediacrylate was in the form of an insoluble and infusible polymer.

The unsaturated esters of Formula 1, in accordance with the invention, can be used as reactive cross-linking agents for unsaturated compounds, or they can serve as intermediates for the preparation of herbicides and insecticides.

The unsaturated esters of Formula I furthermore are very useful for the production of polymers and copolymers containing the structural unit

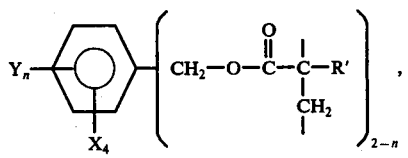

wherein, 4, X, R' and $n$ have the same meaning than in Formula I.

As to diesters, in which is $n = 0$, the para-compounds are preferred. As to monoesters the pentabromo compounds and the pentahalogeno compounds with three and more substituted bromine and two or less substituted chlorine in the aromatic ring are preferred.

These polymers may be produced by means of polymerization processes in solution of organic solvents as benzene or in aqueous suspension or dispersion as well as in substance i.e. essentially without presence of solvents or diluents.

Radical polymerization catalysts as azo compounds like azoisobutyronitrile or peroxides like dibenzoyl or dicumyl peroxide or peroxidisulfate are useful at temperatures of 0 to 150 centigrade celsius.

Where copolymers are produced preferred comonomers are ethylenical unsatureted as styrene, acrylonitrile, acrylic or methacrylic acid esters of 1 to 6 C-atoms in the alcohol group, unsubstituted xylylene acrylates and methacrylates as well as chloro substituted monomers as discribed herein, furthermore butadiene, isoprene, fumaric ar maleinic acids, the polyesters thereof and the anhydride of the latter and other like vinyl chloride and vinylidene chloride.

More than one comonomer may be present, such forming modified terpolymers like bromine containing ABS ore MBS from the acrylates, in case of further acrylic acid esters, acrylonitrile, methacrylic acid esters in presence of styrene on a polymer base of polybutadiene or polyisoprene. Polymers and copolymers so formed are thermoplastic in case of one present acrylic or methacrylic ester group when in formula I is $n = 1$ and are crosslinked and not meltable in presence of two ester groups when in formula I is $n = 0$.

In case of homopolymers and in case of copolymers with high contents of monomer of formula I in the range of 40 to 99,9 wt-% of prepared copolymers bromine contents of 35 to 85, preferred 45 to 75 wt-%, sometimes additionally chlorine being present, are produced, which are very valuable flame retarding additives to polyesters, polyurethanes, polyacetales, ABS and MBS and other polymers.

In case of copolymers of lower contents of 2, preferred 5 to 40 wt % monomers of formula I they itself are valuable flame retardent polymers, especially in cases of bromine contents of 1 to about six or eights wt %.

Both groups of polymers and copolymers are not able to sweep out of polymer products as to high melting points of at least 150° C or their inmeltibility and therefor giving the most valuable attribute to polymer products to have are durable flame retardence for a very long time even at high temperature of surrounding.

Furthermore surprisingly polymers and copolymers are unsulable in all common solvents, so attributing to polymer products a prevention from attack of liquid or gaseous solvents during the use.

Examples for such polymers are polypentabromobenzylacrylate or polytetrabromo mono chloro benzylacrylate and correspenting methacrylates, being polymerizable at e.g. 60°–120° C in methylglycol in presence of e.g. benzoylperoxide (2–6 g per 200 g monomer) in a yeald of 95 to 99 wt.%, containing about 68 to 73 wt. % bromine, being meltable at 200° to 220° C having a low weight loss of 2 % at 206° C during 72 hours.

These polymers in amount of e.g. 10 wt.% can be incorporated in polymers e.g. together with 5 wt.% $Sb_2O_3$ and 30 wt.% glass fiber in 55 wt.% poly-butylenterephthate or poly-ethylen-terephthate.

Products formed thereform beeing superior flame retardent according test of Underwriters Laboratory UL 94, even after worm storage for 7 days at 70° C still having the best value of VO. No sweping out was observed after 7 days storage at 150° C. Other examples for such polymers are polytetrabromoxylylenebisacrylate and -bismethacrylate, both beeing unmeltable, and poly-tetrabromoxylylacrylate which are polymerised in quite similar way and beeing used as flame retardents of the same good behavior.

Polymers and copolymers, and the production thereof such as are described herein, are the subject of application Ser. No. 697,190, filed June 17, 1976, which is assignne to the assignne hereof.

Moreover products of Formula I itself may be added as flame retardents in common plastic products of polymers as mentioned above, polypolyethylene etc.

EXAMPLES

EXAMPLE 1

In a three-necked flask provided with stirrer, reflux condenser and gas feed tube, 75.7 g (1.05 mole) of acrylic acid and 2 g of hydroquinone as polymerization inhibitor are dissolved in 900 ml of ethylene glycol monomethyl ether and 53.3 g (80.503 mole) of anhydrous soda is added portion-wise, with stirring, over a period of 1 hour at room temperature. Then 521 g (1 mole) of pentabromobenzyl chloride is added, the bath temperature is raised to 110° C, and stirring is continued for 2.5 hours at 110° C.

Chloride determination by the Mohr method showed a 96% transformation. Small amounts of undissolved matter were removed by filtration and the reaction solution was allowed to cool. A white, crystalline precipitate of pentabromobenzyl acrylate separated, which was suction filtered, washed chloride-free with water, and vacuum dried at room temperature.

The yield amounted to 368 g of pentabromobenzyl acrylate, corresponding to 66% of the theory. Melting point Fp = 106°-108° C. Determination of the double bond content by the method of Beesing showed the acrylate to have a purity of 97.8%.

EXAMPLE 2

By following the procedure of Example 1, but with the addition of 0.5 mole (246 g) of tetrabromo-p-xylylene dichloride instead of 1 mole of pentabromobenzyl chloride, 261 g of tetrabromo-p-xylylenebisacrylate was obtained as the reaction product, with a melting point of 125°-128° C. The yield amounted to 79% and the purity 97.4% on the basis of double bond determination.

EXAMPLE 3

To a solution of 90.4 g (1.05 moles) of methacrylic acid and 2 g of hydroquinone in 1 liter of methyl glycol, 56.6 g (0.5025 mole) of soda was added, with stirring, under a current of nitrogen, and the mixture was allowed to react for 1 hour at room temperature. After the addition of 521 g (1 mole) of pentabromobenzyl chloride, the mixture was heated for 1 hour at 110° C, with stirring, under a current of nitrogen. The solution was filtered while hot. Upon cooling, pentabromobenzyl methacrylate precipitated as the reaction product. It was suction filtered, washed free of NaCl with water, and dried. Yield 294 g = 51.6%. M.P. 147°-149° C. Beesing analysis for double bond content: 98.2%.

EXAMPLE 4

The procedure was the same as in Example 3, but 0.5 mole (246 g) of tetrabromo-p-xylylene dichloride was added instead of 1 mole of pentabromobenzyl chloride; 282 g of tetrabromo-p-xylylenedimethacrylate was obtained as the reaction product, with a melting point of 129°-132° C. The yield amounted to 82% and the purity, based on double bond determination, was 96.3%.

EXAMPLES 5-22

The examples are summarized in the following table. The new product was obtained by cooling. The new product was recrystallized from isopropanol.

| Example | Product | ml Methyl-glycol | g acid A = Acrylic acid M = Methacrylic acid C = Crotonic acid | g of 47.8% Caustic soda solution | g of tetra-chloroxylyl chloride (m) g of tetra-chloroxylene dichloride (d) | Reaction time, hours | g Crude yield | % Crude yield | Raw product, purity | Recrystal-lization product purity % based on double bond determination | MELTING POINT °C |
|---|---|---|---|---|---|---|---|---|---|---|---|
| 5 | o-Tetrachloro-xylylacrylate | 400 | 63.3 A | 67 | 212 m | 1 | 215 | 89.8 | 93.8 | 97.0 | 63-66.5 |
| 6 | p-Tetrachloro-xylylacrylate | 250 | 39.7 A | 41.9 | 132.5 m | 1 | 120 | 80.3 | 98.2 | 98.8 | 68-70.5 |
| 7 | " | 100 | 14.8 A | 15.6 | 49.3 m | 1 | 45.5 | 82 | 90.7 | 98.5 | 57-9.5 |
| 8 | o-Tetrachloroxyl-ylmethylacrylate | 250 | 47.4 M | 41.9 | 132.5 m | 1 | 149 | 95.6 | 92.4 | 98.0 | 115-7.5 |
| 9 | p-Tetrachloroxyl-ylmethylacrylate | 500 | 94.7 M | 83.7 | 265 m | 1 | 290 | 93 | 95 | 99.7 | 121 |
| 10 | m-Tetrachloroxyl-ylmethacrylate | 250 | 47.4 M | 41.9 | 132.5 m | 1 | 143 | 95.5 | 98 | 99.1 | 82-4.5 |
| 11 | o-Tetrachloroxyl-yl-crotonate | 250 | 45.2 C | 41.9 | 132.5 m | 1 | 150 | 96.2 | 98.5 | 99 | 131-5.5 |
| 12 | m-Tetrachloroxyl-yl-crotonate | 500 | 94.7 C | 83.7 | 265 m | 1 | 281 | 91 | 95.2 | 98.5 | 110.5-15 |
| 13 | p-Tetrachloroxyl-yl-crotonate | 120 | 20.2 C | 19.6 | 67.1 m | 1 | 65.6 | 90.2 | 100 | 100 | 64-71 |
| 14 | o-Tetrachloroxyl-ylene-diacrylate | 250 | 39.7 A | 41.9 | 74.4 d | 0.5 | 67.2 | 73.5 | 97.2 | | 71-4 |
| 15 | m-Tetrachloroxyl-ylene-diacrylate | 1000 | 159 A | 167 | 297.5 d | 1 | 325 | 88.8 | 97.8 | 98.1 | 65.5-67 |
| 16 | p-Tetrachloroxyl-ylene-diacrylate | 500 | 79.3 A | 83.7 | 149 d | 1 | 164 | 89.6 | 99.5 | 99.8 | 117-20 |
| 17 | o-Tetrachloroxyl-ylenedimethacryl-ate | 250 | 47.4 M | 41.9 | 74.4 d | 0.5 | 84 | 86 | 98 | | 67-69 |
| 18 | m-Tetrachloroxyl-ylenedimethacryl-ate | 250 | 47.4 M | 41.9 | 74.4 d | 0.2 | 75 | 76.6 | | 99.7 | 83-5 |
| 19 | p-Tetrachloroxyl-ylenedimethacryl-ate | 500 | 94.7 M | 83.7 | 149 d | 1 | 187 | 95.3 | 98 | 100 | 136.5-38 |
| 20 | o-Tetrachloroxyl-ylenedicrotonate | 250 | 43.1 C | 41.9 | 74.4 d | 1 | 80.3 | 81.9 | 99 | | 80-6 |
| 21 | m-Tetrachloroxyl-ylenedicrotonate | 1000 | 172 C | 167 | 298 d | 1 | 344 | 87.6 | 99 | | 75.5-79 |
| 22 | p-Tetrachloroxyl-ylenedicrotonate | 500 | 94.7 C | 83.7 | 149 d | 1 | 183 | 93.5 | 98 | 98.8 | 158-62 |

EXAMPLE 23

Tetrachloro-p-xylylene diacrylate 14.7 g of sodium carbonate (0.14 mole) was added portion-wise, with stirring, and under a current of $N_2$, to 20.3 g of acrylic acid (0.28 mole) plus 1 g of hydroquinone in 200 ml of dimethylformamide at 60°. After dissolution had taken place, the solution was heated with 41.7 g of tetrachloro-p-xylylene chloride (0.132 mole) for 1 hour at 120° C. Then 700 ml of water was added; the crystallizate was suction filtered, washed free of NaCl and dried.

Crude yield 50.2 g (98% of the theory)
Purity 98.5%
Melting point: 116°–121°

EXAMPLE 24

Tetrachloro-p-xylylene diacrylate

To 55.5 g of acrylic acid (0.77 mole) plus 0.5 g of hydroquinone in 875 ml of methanol 188 ml of a 3.72N methanolic $NaOCH_3$ solution (0.7 mole) was gradually added, with stirring, under a current of nitrogen. The methanolic sodium acrylate solution thus obtained was heated with 104 g of tetrachloro-p-xylylene chloride (0.33 mole) for 1 hour in an autoclave equipped with a stirrer. After the mixture had cooled, the crystallizate was suction filtered, washed free of NaCl, and dried.

Crude yield 66.3 g (51.3% of the theory)
Purity 97.5%
Melting point: 106°–119°

EXAMPLE 25

Tetrachloro-p-xylylene diacrylate

To a solution of 72.1 g of acrylic acid (1 mole) in 500 ml of methyl glycol plus 0.8 g of hydroquinone, a 47.8% caustic soda solution was added drop by drop, with stirring, under a current of nitrogen, until the pH was 6. Approximately 83 g (1 mole) was used. After the addition of 148.8 g of tetrachloro-p-xylylene chloride (0.475 mole), the mixture was refluxed with stirring, under a current of nitrogen, for 1 hour, and was suction filtered while hot. The precipitate was washed free of NaCl with water and dried. 64 g of insoluble and infusible product, i.e., 35% of the theory, of polymeric tetrachloro-p-xylylenediacrylate was obtained. 102 g of monomeric tetrachloro-p-xylylenediacrylate was obtained from the filtrate, i.e., 55% of the theory, purity 98%.

What is claimed is:

1. Compound of the formula:

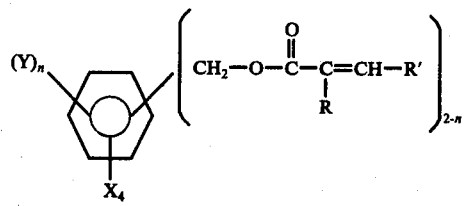

wherein:
each X is chloro or bromo
Y is methyl or bromo
n is 0 or 1
each of R and R' is hydrogen or methyl 2. Compound of claim 1, wherein R and R' is each hydrogen.

3. Compound of claim 1, wherein R is methyl and R' is hydrogen.

4. Compound of claim 1, wherein R is hydrogen and R' is methyl.

5. Compound of claim 1, wherein n is 0 and the ester groups are in para positions.

6. Compound of claim 5, wherein R and R' is each hydrogen.

7. Compound of claim 5, wherein R is methyl and R' is hydrogen.

8. Compound of claim 5, wherein R is hydrogen and R' is methyl.

* * * * *

UNITED STATES PATENT AND TRADEMARK OFFICE
CERTIFICATE OF CORRECTION

PATENT NO. : 4,059,618
DATED : November 22, 1977
INVENTOR(S) : Georg Blumenfeld, Hermann Richtzenhain, Wilhelm Vogt and Norbert Volkommer It is certified that error appears in the above-identified patent and that said Letters Patent are hereby corrected as shown below:

First page, [30], change "Feb.27, 1974" to --Feb. 27, 1975-- change "2408468" to --2508468--.

Column 5, line 18, change "(80.503 mole)" to --(0.503 mole)--.

Signed and Sealed this

Sixth Day of June 1978

[SEAL]

Attest:

RUTH C. MASON
Attesting Officer

DONALD W. BANNER
Commissioner of Patents and Trademarks